(12) United States Patent
Casey

(10) Patent No.: US 11,628,282 B2
(45) Date of Patent: Apr. 18, 2023

(54) NO PREPARATION BALLOON GUIDE CATHETER

(71) Applicant: NEURAVI LIMITED, Galway (IE)

(72) Inventor: Brendan Casey, Galway (IE)

(73) Assignee: NEURAVI LIMITED, Galway (IE)

( * ) Notice: Subject to any disclaimer, the term of this patent is extended or adjusted under 35 U.S.C. 154(b) by 571 days.

(21) Appl. No.: 16/694,574

(22) Filed: Nov. 25, 2019

(65) Prior Publication Data

US 2021/0154443 A1    May 27, 2021

(51) Int. Cl.
A61M 25/10    (2013.01)

(52) U.S. Cl.
CPC ...... *A61M 25/104* (2013.01); *A61M 25/1025* (2013.01); *A61M 2025/109* (2013.01); *A61M 2025/1061* (2013.01)

(58) Field of Classification Search
CPC ............ A61M 25/104; A61M 25/1025; A61M 2025/1061; A61M 2025/109; A61M 25/0102; A61M 25/1018; A61M 2025/1077; A61B 2017/22051
See application file for complete search history.

(56) References Cited

U.S. PATENT DOCUMENTS

| | | |
|---|---|---|
| 3,402,718 A | 9/1968 | Doherty |
| 3,742,960 A | 7/1973 | Binard |
| 4,019,515 A | 4/1977 | Kornblum et al. |
| 4,596,554 A | 6/1986 | Dastgeer |
| 5,141,518 A | 8/1992 | Hess et al. |
| 5,466,222 A | 11/1995 | Ressemann et al. |
| 5,647,847 A * | 7/1997 | Lafontaine ...... A61M 25/10188 604/100.03 |
| 6,217,503 B1 | 4/2001 | Weinberger et al. |
| 6,217,547 B1 | 4/2001 | Lee |

(Continued)

FOREIGN PATENT DOCUMENTS

| | | |
|---|---|---|
| EP | 0 710 490 A2 | 5/1996 |
| EP | 2 572 749 A2 | 3/2013 |
| WO | 2018/033401 A1 | 2/2018 |

OTHER PUBLICATIONS

Extended European Search Report issued in corresponding European Patent Application No. 20 20 9451 dated May 21, 2021.

*Primary Examiner* — Theodore J Stigell
*Assistant Examiner* — Rachel T. Smith
(74) *Attorney, Agent, or Firm* — Troutman Pepper Hamilton Sanders LLP

(57) ABSTRACT

A system has a balloon guide catheter for use in mechanical thrombectomy procedures which requires very little preparation to inflate the balloon compared to most contemporary designs. The balloon guide catheter can have an elongated tubular member and a proximal luer. The elongated tubular member of the catheter can have two internal lumens. A first inner hollow lumen can have a large opening for aspiration and the advancement of auxiliary devices, and a second inflation lumen can provide a fluidic passageway to inflate the balloon. The proximal luer can have a luer lumen, an inflation port, and a mandrel hub. A removable mandrel can extend distally from the mandrel hub to occupy the full length and volume of the inflation lumen of the tubular member. A tab of the mandrel can extend external to the luer to facilitate removal of the mandrel from the catheter prior to inflating the balloon.

20 Claims, 7 Drawing Sheets

(56) References Cited

U.S. PATENT DOCUMENTS

| | | |
|---|---|---|
| 6,391,037 B1 | 5/2002 | Greenhalgh |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 2005/0197667 A1 | 9/2005 | Chan et al. |
| 2006/0064151 A1 | 3/2006 | Guterman |
| 2006/0276746 A1 | 12/2006 | Burnside et al. |
| 2007/0073269 A1 | 3/2007 | Becker |
| 2008/0281350 A1 | 11/2008 | Sepetka |
| 2010/0324649 A1 | 12/2010 | Mattsson et al. |
| 2011/0118546 A1* | 5/2011 | Dillon ............ A61M 25/10186 600/116 |
| 2012/0232477 A1 | 9/2012 | Schaeffer |
| 2012/0283768 A1 | 11/2012 | Cox et al. |
| 2013/0253417 A1* | 9/2013 | Dinh ................ A61M 25/0053 604/509 |
| 2014/0135812 A1 | 5/2014 | Divino et al. |
| 2014/0200607 A1 | 7/2014 | Sepetka et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

\* cited by examiner

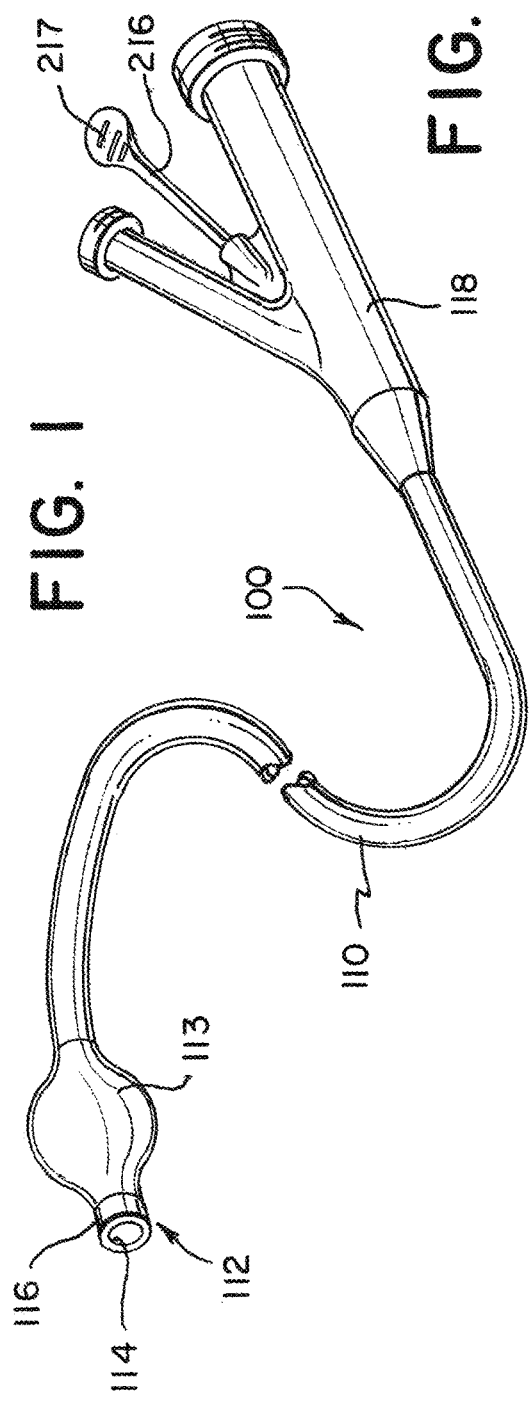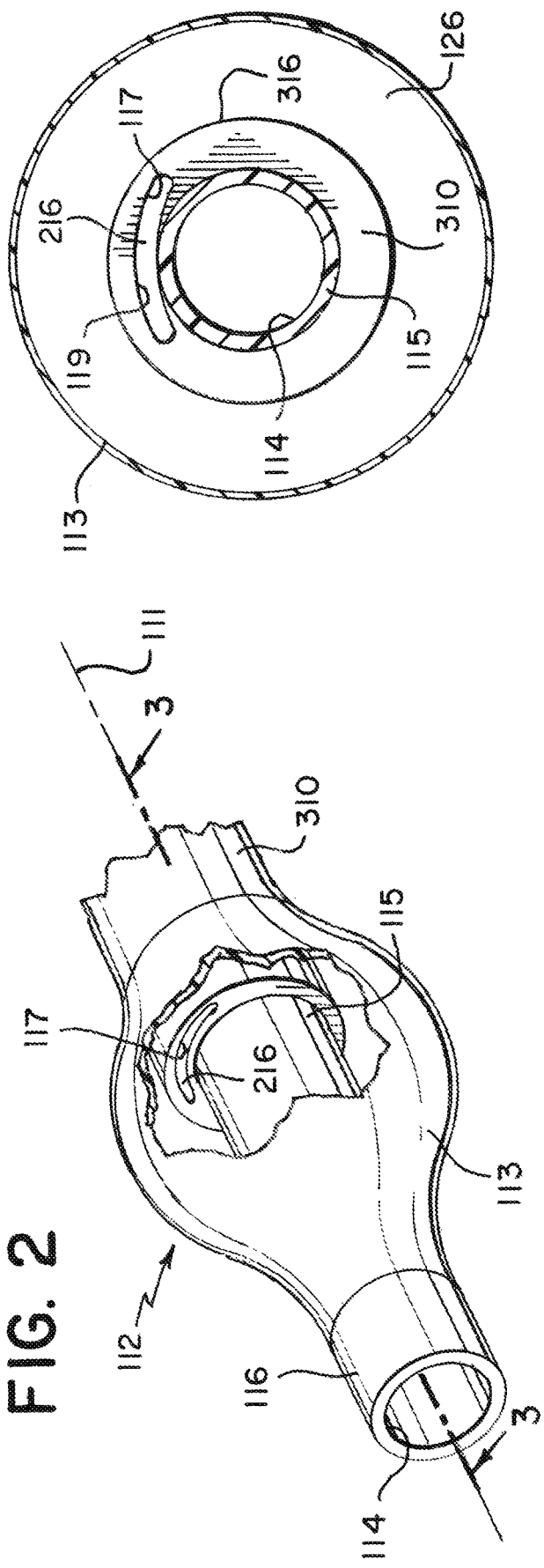

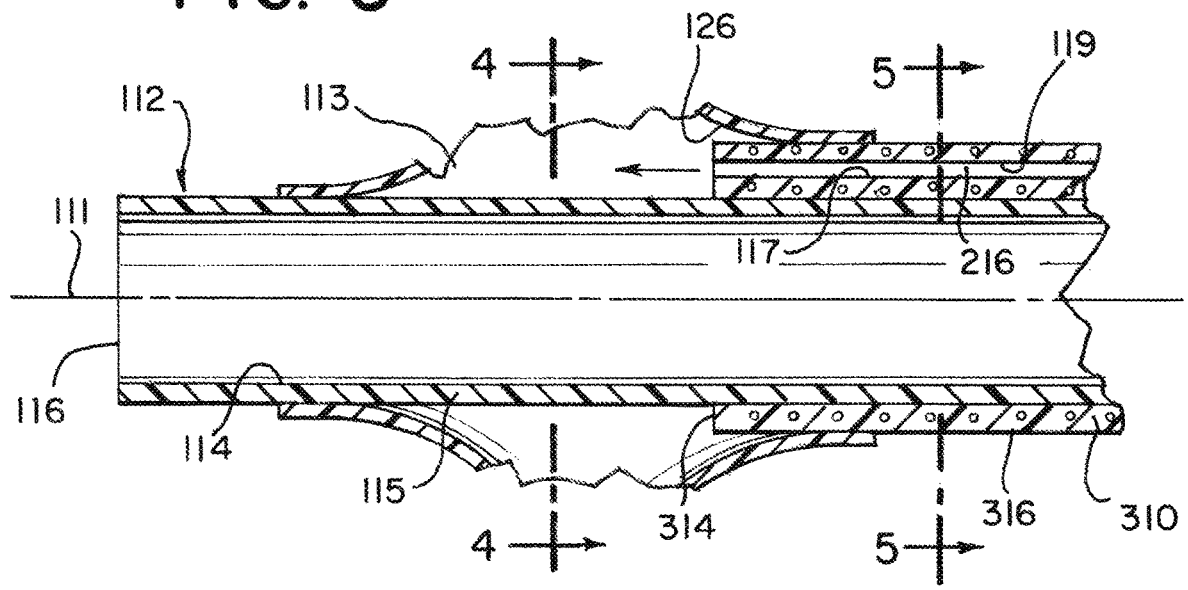
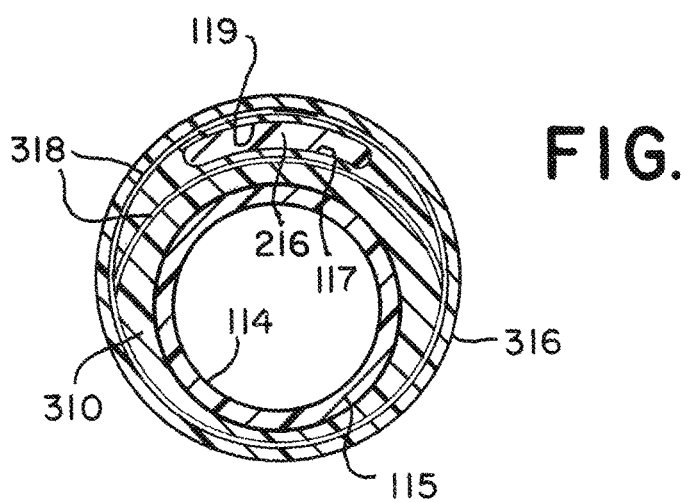
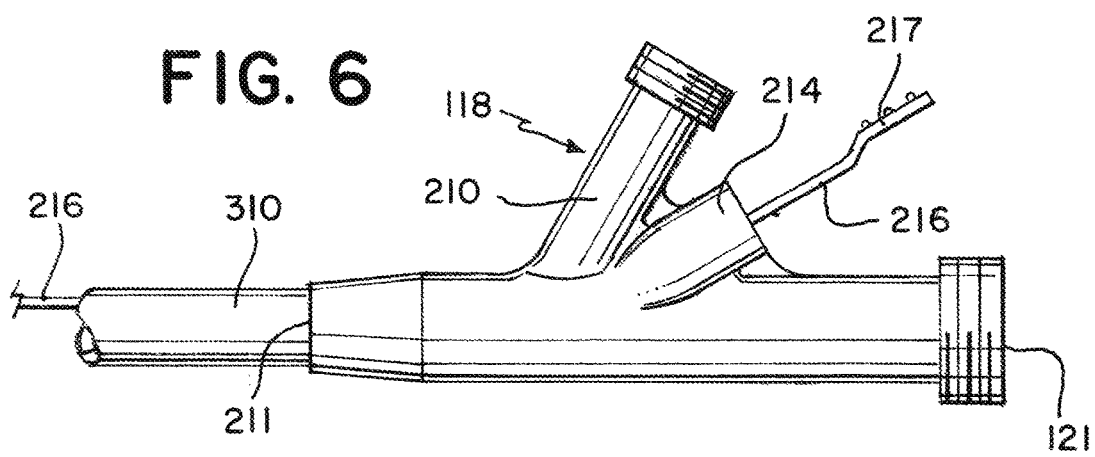

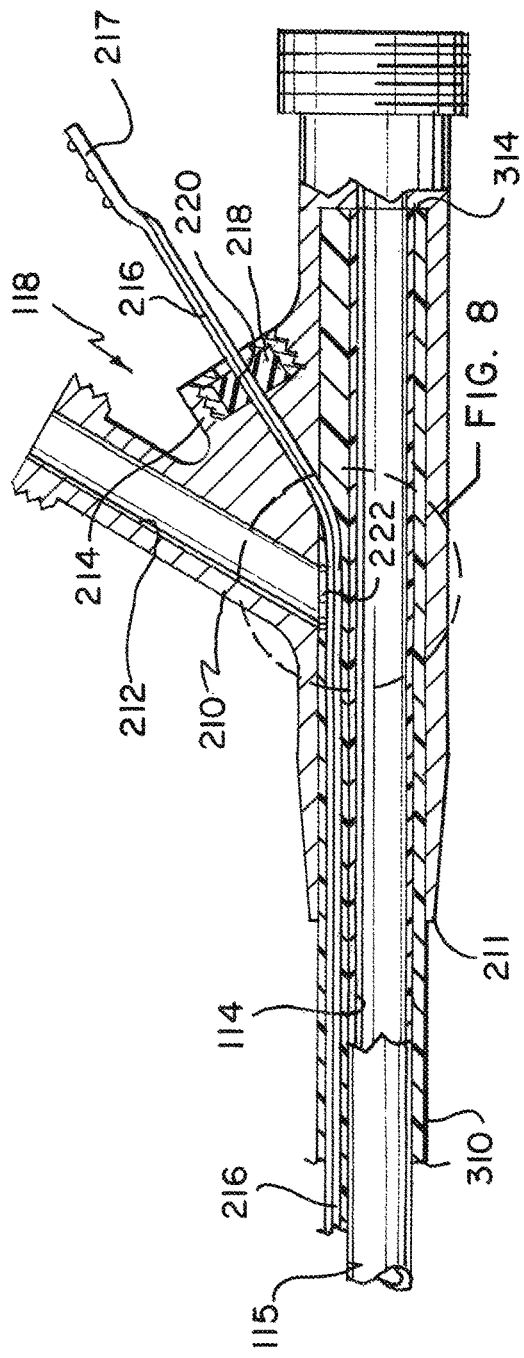
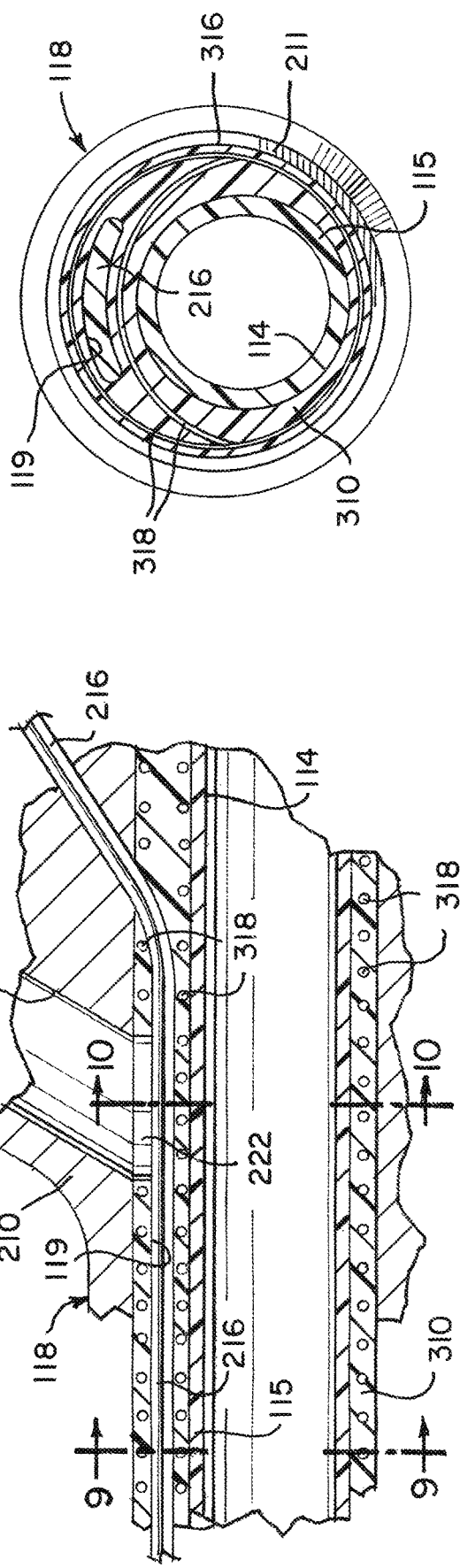
FIG. 7
FIG. 8
FIG. 9

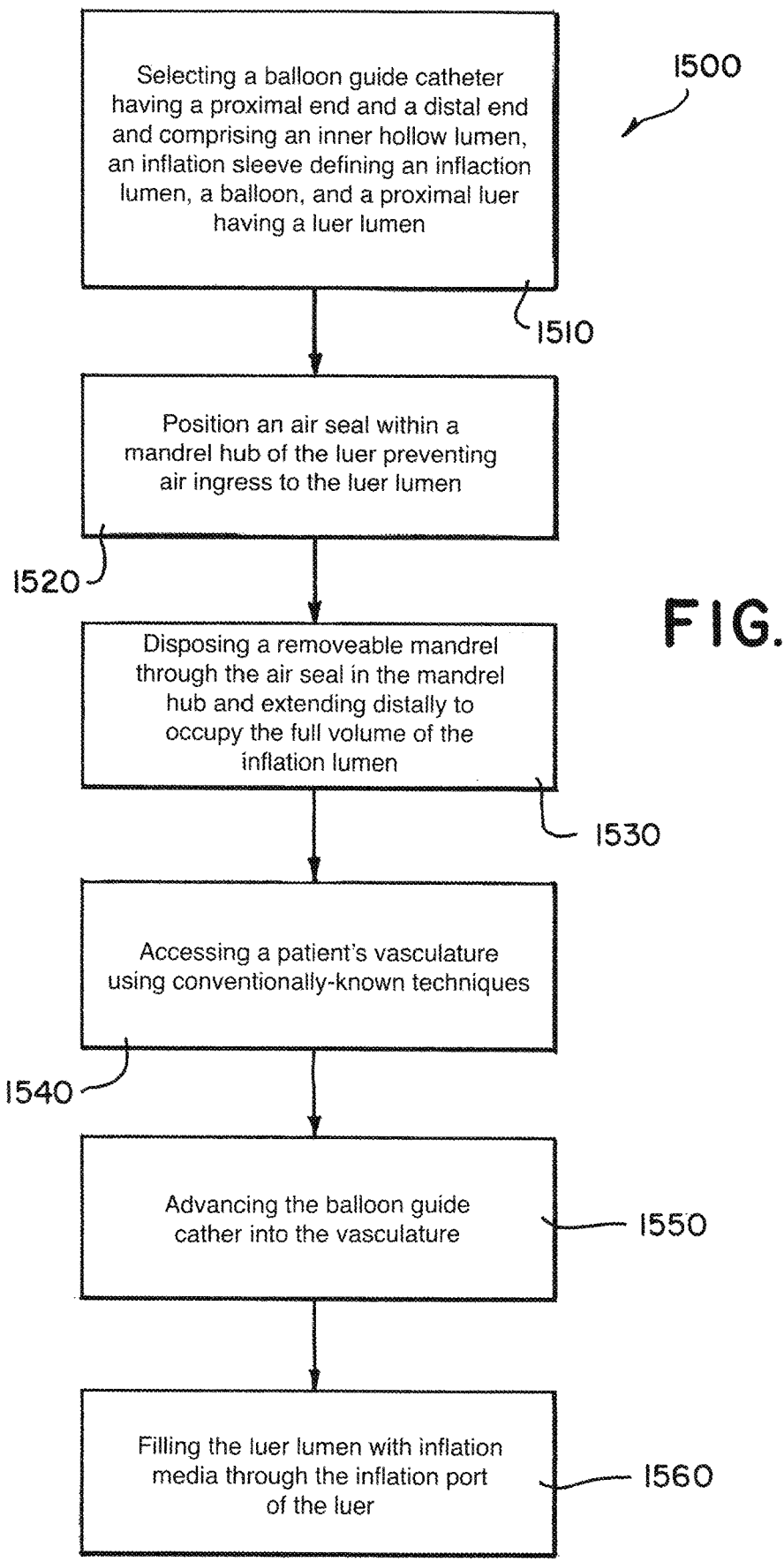

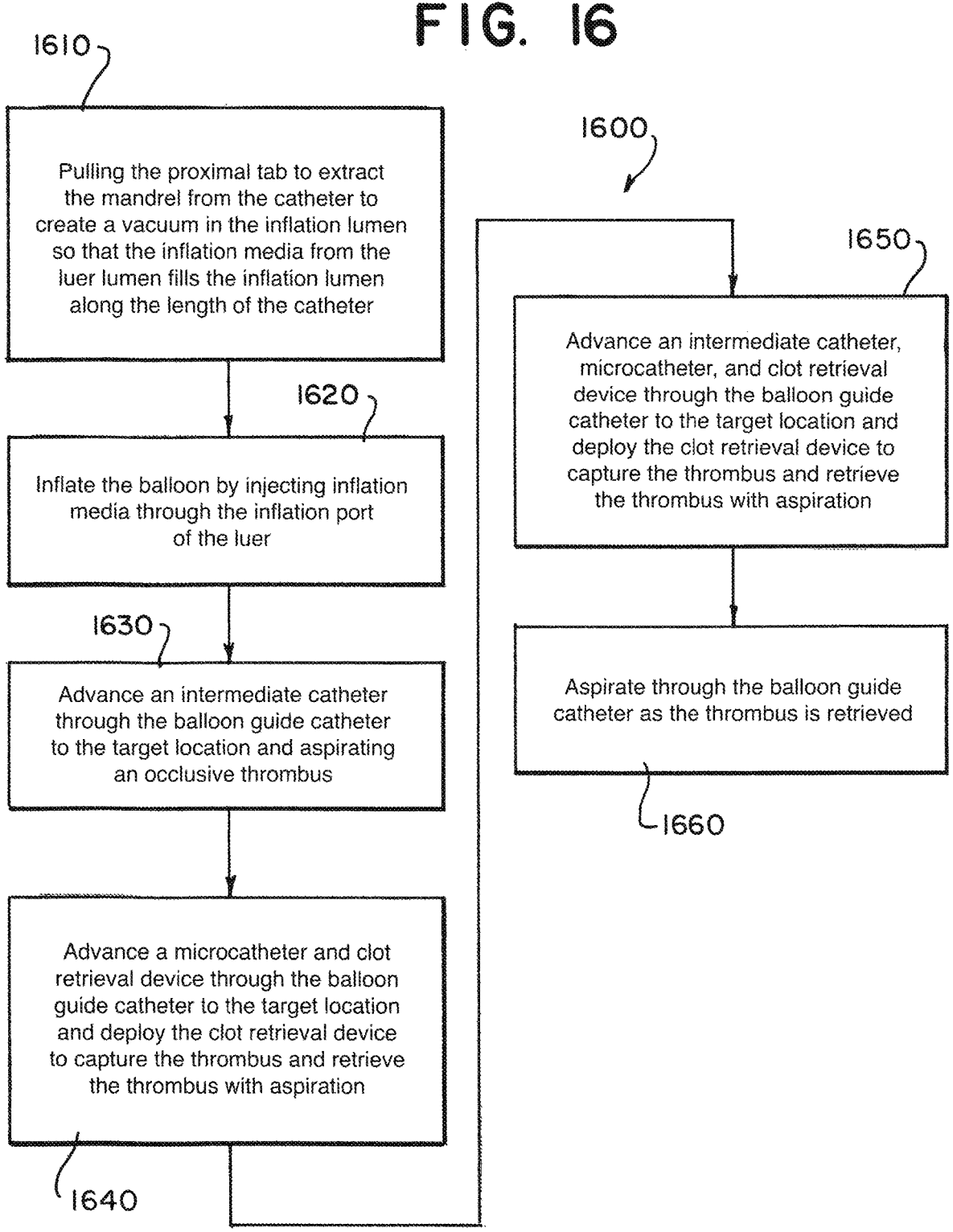

NO PREPARATION BALLOON GUIDE CATHETER

FIELD OF THE INVENTION

The present invention generally relates devices and methods used in removing acute blockages from blood vessels during intravascular medical treatments. More specifically, the present invention relates to balloon guide catheters used to occlude portions of target blood vessels during such procedures.

BACKGROUND

Catheters can be hollow, flexible structures used for a variety of applications and procedures within a patient's vasculature. In many cases, catheters can be directed to a target area in a particular vessel and then serve as a guide for other conventional and more specialized devices to access the area through its lumen. Such devices can include microcatheters, guidewires, clot retrieval devices, aspiration catheters, or any of a number of other commercially-available accessory components.

Balloon guide catheters can be used in standard arterial or in ischemic stroke procedures to act as a conduit for diagnostic and therapeutic devices while also to providing flow arrest, flow control, and/or flow reversal to aid in the safe retrieval of a clot from the patient. This flow control provides distal vascular protection which is important to minimize the risk of emboli migration and other procedural complications, particularly in the small and fragile cerebral passages for stroke patients. Additionally, proximal flow control provided by these catheters has been shown to correlate with better angiographic and clinical outcomes. These catheters are useful for reducing procedure times and effort during the recanalization process of intra-arterial mechanical thrombectomy procedures. They can limit the number of clot retrieval attempts needed during ischemic stroke, for example, while also reducing the occurrence of distal emboli.

A balloon guide catheter must be sufficiently flexible while also having the axial stiffness to be delivered smoothly through tortuous vasculature to the target site (typically the internal carotid artery and on into the cerebral vasculature for ischemic stroke patients). The devices must also be designed to be as atraumatic as possible while still delivering a high level of performance. Once access to the target is gained and the balloon deployed, the guide catheter has to be appreciably robust to remain stable in that position while other devices are advanced, manipulated and withdrawn through the lumen. The lumen itself must be of a large enough diameter for these devices while also directing more efficient aspiration necessary to remove blood and thrombus material during the procedure. However, the lumen size must be balanced by the need for an outer diameter as low profile as possible to minimize the size of the entry orifice that must be closed once the catheters are removed from the patient.

While current designs must balance these tradeoffs, one of the most significant challenges, and one which prevents more widespread adoption of these catheters, is the process of preparing the catheter for use. Currently, prior to introducing a balloon guide catheter into the vasculature, the physician must flush the balloon and purge the system of air before any inflation media can be introduced. The current practices employed to remove air from the inflation lumen of existing catheters are laboriously slow and frustrating and can lead to substantial waste. Additionally, it can be difficult to tell the difference between a "significantly-purged" and a "completely-purged" system. However, failure to complete the purging process can result in complications such as cavitation, uneven inflation, and the release of trapped air pockets in the event of a balloon rupture during the procedure. These incidents have the potential to cause neurological defects or other complications.

Currently, the typical steps to purge most balloon guide catheter systems involve first connecting a stopcock to a proximal port fitting of the catheter. A syringe is partially filled with a contrast media or other liquid and connected to the stopcock. The syringe plunger is then actuated and held to aspirate the inflation lumen and balloon of the catheter. Trapped air in the form of bubbles are drawn into the liquid of the syringe during this process. The evacuated inflation lumen is allowed to fill with the contrast media in the syringe by releasing the plunger. This procedure is repeated until no more bubbles are observed during aspiration. A separate syringe can then be attached to the stopcock and used to inject contrast media, inflating the balloon. The balloon can then be inspected for leakage or other defects. A syringe can then be used to deflate the balloon so that it can be inserted into the vasculature. In some cases, bubbles persist to the point where the balloon guide catheter must be discarded and a new one procured and prepared. This acrimonious process requires care and can frustrate the user, as well as adding considerable time to the overall duration of the thrombectomy procedure. The result can be a reluctance to adopt and use these devices during operations where their benefits could otherwise improve patient outcomes.

The need for shorter groin puncture to reperfusion times is always present in order to limit lasting damage, particularly in ischemic stroke patients. The present design is aimed at providing an improved balloon guide catheter which addresses the stated deficiencies and gives the user much greater flexibility during the procedure.

SUMMARY

It is an object of the present design to provide systems, devices, and methods to meet the above-stated needs. Having a balloon guide catheter that does not require the physician to conduct the cumbersome preparatory steps prior to use, as is presented in the current design, can greatly reduce procedure times and thus result in better clinical outcomes.

The current design facilitates the preparation of the balloon guide catheter prior to balloon inflation in a mechanical thrombectomy procedure. The design accomplishes this objective through integrating a removable mandrel into the catheter, which serves to occupy the nominal volume of an inflating lumen prior to inflating the balloon. By occluding the lumen, the mandrel precludes the presence of trapped gas within the system which would otherwise require evacuation prior to a medical procedure. When the physician is ready to inflate the balloon, the mandrel can be withdrawn from the system, thereby drawing a vacuum in the inflation lumen. In the absence of trapped gas, the balloon can then be inflated using conventionally-known techniques.

Disclosed herein are various exemplary devices and methods for minimizing the preparation needed for inflating the balloon of balloon guide catheters. In addition, the disclosed devices address other drawbacks of the art, such as lumen kink protection and maximizing clot retrieval effectiveness.

The systems can generally include a balloon guide catheter having a tubular inner core with an inner hollow catheter lumen. An elongated tubular member can be disposed around but not concentric with the inner core. The elongated tubular member can have a proximal end, a distal end proximal of the distal end of the inner core, and a separate inflation sleeve defining an inflation lumen independent of the inner hollow lumen. The inner hollow lumen can extend between the proximal end and the distal end of the inner core. The inner hollow lumen can be sized to maximize clot retrieval capabilities, and be a conduit for microcatheters, guidewires, clot retrieval devices, aspiration catheters, or any of a number of other commercially-available accessory devices. The inflation lumen can extend the majority of the length of the inner core, from an inflation port at the proximal end to the inside of a balloon at the distal end of the elongated tubular member. The balloon can be affixed to a distal portion of the tubular inner core and can also be affixed near the distal end of the elongated tubular member.

Approximate the proximal end of the catheter can be a luer having a proximal end, a distal end integral with the elongated tubular member, and an internal luer lumen. The luer can further have an inflation inlet providing a passageway fluidically linking the luer lumen to the inflation lumen of the elongated tubular member. The luer can have an inflation port and a mandrel hub, both of which can be in communication with the internal luer lumen.

The mandrel hub of the luer can have a proximal port with a mandrel disposed therethrough and extending distally from the port the full length of the inflation sleeve. The mandrel can be removably disposed within the mandrel hub of the luer and the inflation sleeve. The mandrel can have a distal end and an opposing proximal end which can include a mandrel tab. The mandrel tab can extend proximal to the proximal port and external to the luer. The mandrel is sized such that it occludes the inflation lumen and occupies the full internal volume thereof. The mandrel can have a protracted dimension to extend the distance between the mandrel hub and the balloon approximate the distal end of the balloon guide catheter. The proximal port of the mandrel hub can further have an air seal which the mandrel passes through. The air seal prevents air ingress to the luer lumen and inflation lumen whether or not the mandrel is present.

The lumen of the inflation sleeve is in fluidic communication with the balloon and can serve as a channel for inflating and deflating the balloon. The inflation sleeve can have any of a number of shapes, but in general, has a smaller cross-section than the inner hollow lumen. In one example, the inflation sleeve comprises a substantially crescent-shaped cross-section. The inflation sleeve can be formed from Polyethylene (PE), Polyethylene terephthalate (PET), Polytetrafluoroethylene (PTFE), or a similar fluoropolymer.

Tortuosity can induce forces on the body of the catheter, and, in cases of extreme or abrupt angulation, it is possible for one or more of the inner catheter lumen or inflation lumen to become kinked. A kinked inner hollow lumen can constrain or completely impede the movement or operation of other devices therein. A kinked inflation lumen can inhibit flow to or from the balloon near the distal end of the catheter. These situations create complications during a treatment, as a non-functioning balloon guide catheter may need to be removed, with the physician then forced to conduct the procedure without blood flow arrest, or a further tube inserted through the inflation lumen to deflate the balloon. These situations also add time to the procedure.

To reduce the likelihood of kinking, the elongated tubular member could, for example, have a system of reinforcing wires or braids to support and secure the inner hollow lumen and the inflation lumen. The wire system can be embedded within the catheter and wrapped around the lumens to protect the inflation lumen and inner hollow lumen along at least a portion of the length of the elongated tubular member. The wires can also enhance the torque capabilities along the length of the catheter, while protecting the inflation lumen from kinks. The wire system could be present above and/or around the inflation sleeve and can tie the sleeve radially to the inner core. The mesh system can be a braided wire network or some similar structure that would improve the strength of the catheter while reducing its overall stiffness. In other wire configurations, such as coiled, it could be possible to introduce stiffness gradients along various lengths of the catheter. The strength and flexibility could also be influenced if the individual wires had a round, square, or some other shaped profile.

Another system for preparing a balloon guide catheter can comprise an elongated tubular member, a proximal luer, and a seamless balloon.

The elongated tubular member can have a proximal end, a distal end, an outer surface, and two inner surfaces. A first inner surface can define an inner hollow lumen extending between the proximal end and the distal end of the elongated tubular member for the delivery of other catheters and/or devices to a target site. A second inner surface can define an inflation lumen extending at least a portion of the length between the proximal end and the distal end of the elongated tubular member. The inflation lumen can be at least partially eccentric to the elongated tubular member and inner hollow lumen. Similar to other examples, a reinforcing braid or wire network can be disposed around the outer surfaces of the inner hollow lumen and the outer surfaces of the inflation lumen to provide kink protection. The inflation lumen and can have a cross-section the shape of an arc or crescent, and an area smaller than that of the inner hollow lumen, allowing the inflation lumen to be positioned off-center and nearer to an outer edge of the elongated tubular member. This shape of the inflation lumen allows the larger inner hollow lumen to occupy most of the cross-sectional area of the elongated tubular member, thereby improving the deliverability of other devices and improving aspiration efficiency.

The proximal luer can comprise an inner lumen, an inflation port sized to receive fluid injection, a mandrel hub sized to receive a mandrel, and an air seal disposed within the mandrel hub preventing air ingress to the inflation lumen of the elongated tubular member. The mandrel can be removably disposed within the mandrel hub and extends in to and through the inflation sleeve via an inlet approximate the proximal end of the elongated tubular member. The inlet can provide a fluid passage way through the outer wall of the elongated tubular member between the inflation lumen and the luer lumen.

The mandrel can be sized to fully occlude the full length and volume of the inflation lumen, such that no pre-existing gas exists within the inflation lumen which could require repeated evacuation attempts to prepare the balloon for inflation. The occluding distal portion of the mandrel can have a protracted length to span the distance between the proximal port of the mandrel hub and the balloon at the distal end of the elongated tubular member. The proximal end of the mandrel can comprise a tab extending external to the luer and can be used by the user to grip and extract the mandrel body from the system when the physician is ready to inflate the balloon.

A seamless balloon can be secured to the distal end of the elongated tubular member. The balloon can be joined to the elongated tubular member by a mechanical member, such as a ring-shaped tie band, or be attached by an adhesive or other means. The balloon can be made soft and extremely compliant by choosing particular materials for construction, such as silicone, an elastomeric alloy, or a blend of similar materials. When inflated, the balloon can provide a means of securing the position of the catheter in the vasculature. In addition, the balloon is capable of arresting the blood flow, thereby improving the efficiency of any aspiration directed through the inner lumen of the balloon guide catheter and/or other associated catheters used in conjunction with the balloon guide catheter. The aspiration can be used to retrieve clots and prevent clot fragments from migrating distally, potentially resulting in the embolization of downstream distal vessels.

The larger inner hollow lumen of the elongated tubular member provides an easier conduit for the transmission of auxiliary products to the target site, such as intermediate or aspiration catheters, microcatheters, and clot retrieval devices. The large mouth opening to the lumen also simplifies the retraction of such devices with captured clots.

Also provided is a method for utilizing a balloon guide catheter system that requires minimal preparation to inflate the balloon. The method can have some or all of the following steps and variations thereof, and the steps are recited in no particular order.

A system with a balloon guide catheter can be selected. The balloon guide catheter can have a proximal end, a distal end, an inner hollow lumen, an inflation sleeve defining an inflation lumen, a balloon, and a proximal luer. The luer can comprise an injection port, a mandrel hub, and a luer lumen in fluidic communication with the inflation lumen.

An air seal can be provided at the proximal end of the mandrel hub which prevents air ingress into the luer lumen. A removeable mandrel can be disposed through the air seal in the mandrel hub and extend distally to occlude the full volume of the inflation lumen.

Access to the patient's vasculature is obtained using conventionally-known techniques and the balloon guide catheter can be advanced into the vasculature to a location proximal a target site. The luer lumen can be filled with inflation media liquid through the inflation port of the luer using a syringe or other inflation source. The liquid media is typically a contrast solution, saline, or a mixture of the two. A proximal tab can then be pulled to extract the mandrel from the catheter to draw a vacuum in the inflation lumen, allowing the inflation media in the luer lumen to fill the inflation lumen along the length of the catheter. The balloon can be inflated by injecting additional inflation media from the inflation source.

The method can further include steps where other devices are used in concert with the balloon guide catheter. For example, a mechanical thrombectomy procedure can be performed using known techniques from the art. Any number of commercial products are available for these procedures and thus the method is not limited to those mentioned here.

A step could involve an intermediate or aspiration catheter advanced to the target site through the inner lumen of the balloon guide catheter to aspirate an occlusive thrombus into the mouth of the catheter. Similarly, an alternative step could utilize a microcatheter with a clot retrieval device advanced through the lumen of the balloon guide catheter. The microcatheter can be advanced across an occlusive thrombus and the clot retrieval device deployed to capture and retrieve the thrombus with aspiration through the balloon guide catheter. In a further example, a microcatheter with a clot retrieval device can have an access or intermediate catheter as an outer sheath. The intermediate catheter, microcatheter, and clot retrieval device can be advanced to the target site together through the lumen of the balloon guide catheter. The clot retrieval device can then capture and retrieve the thrombus.

In any of the foregoing examples, aspiration can be directed through any combination of the balloon guide catheter, intermediate catheter, or other associated aspirating catheters where used during retrieval of the thrombus.

The balloon can be deflated by providing suction at the inflation port of the luer to withdraw the inflation media. Upon completion of the procedure, the system can be withdrawn from the vasculature.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with the following description of the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combining elements from multiple figures to better suit the needs of the user.

FIG. 1 is an illustration of a system having a balloon guide catheter according to aspects of the present invention;

FIG. 2 shows a closer isometric cutaway view of the distal tip of the balloon guide catheter with the balloon inflated according to aspects of the present invention;

FIG. 3 shows a side cross-section view of the tip of the balloon guide catheter from FIG. 2 according to aspects of the present invention;

FIG. 4 is a cross-section view of the catheter tip from FIG. 3 according to aspects of the present invention;

FIG. 5 is another cross-section view of the catheter tip from FIG. 3 showing the internal lumens according to aspects of the present invention;

FIG. 6 is a side view of a proximal luer of the balloon guide catheter according to aspects of the present invention;

FIG. 7 is a cross-section view the luer from FIG. 6 with the mandrel showing the internal flow paths according to aspects of the present invention;

FIG. 8 is an inset detail view of the area around the inflation inlet from FIG. 7 with the mandrel according to aspects of the present invention;

FIG. 9 is a cross-section view from FIG. 8 from downstream of the inflation inlet with the mandrel occluding the inflation lumen according to aspects of the present invention;

FIGS. 15-16 are flow diagrams outlining one possible method for using the system according to aspects of the present invention.

DETAILED DESCRIPTION

Figure 10:
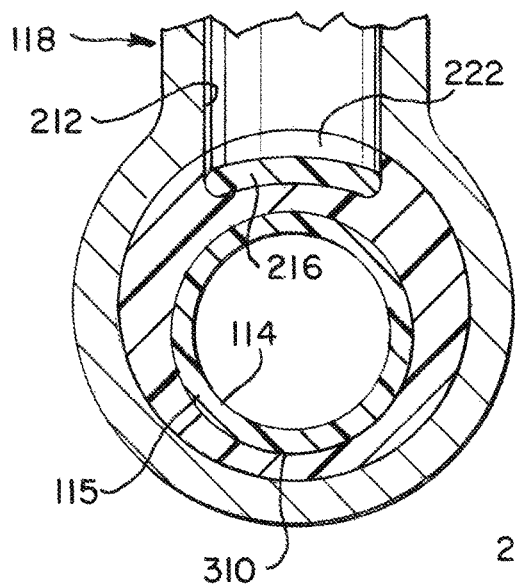
FIG. 10 is another cross-section view from FIG. 8 at the inflation inlet according to aspects of the present invention.

Specific examples of the present invention are now described in detail with reference to the Figures, where identical reference numbers indicate elements which are functionally similar or identical. The examples address many of the deficiencies associated with preparing a traditional balloon guide catheter for inflation of the balloon, with the removal of steps and processes which can result in significant reductions to procedure times and waste.

Accessing the various vessels within the vasculature, whether they are coronary, pulmonary, or cerebral, involves well-known procedural steps and the use of a number of conventional, commercially-available accessory products. These products, such as angiographic materials, rotating hemostasis valves, and guidewires are widely used in laboratory and medical procedures. When these products are employed in conjunction with the system and methods of this invention in the description below, their function and exact constitution are not described in detail.

Referring to the figures, in FIG. 1 there is illustrated a system 100 for preparing a balloon guide catheter 110 for use in a procedure. As illustrated, the catheter 110 of the system can have a proximal luer 118, an inner hollow lumen 114, a removeable mandrel 216, and a catheter tip 112 approximate the distal end 116 of the catheter. The inner hollow lumen can be used for the delivery of other catheters and auxiliary devices to the target site, while also providing a channel for aspiration and the injection of contrast. The size of the lumen can vary based on the target site, or a standard guide catheter inner diameter of approximately 0.087" can be used. The luer can be formed integrally with, or could be bonded, to the distal tubular body of the catheter.

FIG. 2 shows an isometric cutaway view of the catheter tip 112 of the balloon guide catheter from FIG. 1. The catheter body has an elongated tubular member 310 disposed around a tubular inner core 115. The inner core can be relatively thin walled such that an inner hollow lumen 114 extending therethrough can have a large cross-sectional area for aspiration and the passage of other devices. The inner hollow lumen can define a longitudinal axis 111 such that the elongated tubular member 310 is at least partially eccentric to the inner core 115 and the longitudinal axis 111. The smaller diameter of the inner core compared to the diameter of the elongated tubular member allows the balloon to be flush mounted with the transverse profile of the catheter when the balloon is deflated. Flush mounting provides a smoother delivery profile for the catheter. The balloon 113 can be affixed at its proximal end to the elongated tubular member 310 and at its distal end to the inner core 115.

The elongated tubular member 310 has an inflation lumen 117 running parallel to the longitudinal axis 111 which can terminate at the distal end of the elongated tubular member inside the interior of the balloon 113. The elongated tubular member and inflation lumen can extend a majority of the length of the inner core 115. Prior to inflation of the balloon, the mandrel 216 occupies the inflation lumen extending from the interior of the proximal luer 118 to the distal end of the elongated tubular member 310. The inflation lumen can be smaller than the inner hollow lumen, as the volume of inflation media necessary to inflate the balloon is typically not substantial. The inflation lumen can be a crescent shape and can assume a cross-sectional area of approximately or about 0.2 mm$^2$. This shape of the inflation lumen maximizes the internal space of the elongated tubular member 310 for the inner hollow lumen 114 to occupy most of the cross-section. The large internal diameter of the inner hollow lumen facilitates the delivery of equipment, contrast, and more efficient aspiration.

When elements described and visualized in the figures as a tubular structure and generally illustrated as a substantially right cylindrical structure, when used herein, the terms "tubular" and "tube" are to be construed broadly. They are not meant to be limited to a structure that is a right cylinder or strictly circumferential in cross-section or of a uniform cross-section throughout its length.

A side view of the distal catheter tip 112 of the balloon guide catheter is shown in FIG. 3. The inner hollow lumen 114 can run longitudinally with the inflation lumen 117 of the inflation sleeve 119 and terminate at the distal end 116 of the inner core 115. The inflation lumen can run the full length of the elongated tubular member 310 to the distal end 316 and empty in to the balloon lumen 126. The inflation media fluid, often a 50/50 contrast mix, can be injected into the proximal luer providing a fluidic flow into the inflation lumen. Fluid can be flowed through the length of the inflation lumen and in to the balloon lumen as indicated by the arrows.

The balloon 113 can take on an ovular or tapered shape when inflated, with an atraumatically large, flared radius of curvature for interfacing with the vasculature walls. The balloon can be secured to the distal end of the elongated tubular member. The balloon can be joined to the outer surface 316 of the elongated tubular member 310 by a mechanical member, such as a ring-shaped tie band or strap, or it could be crimped, welded, or attached by other means. In one example, the balloon is attached using suitable adhesive means, such as epoxy or cyanoacrylate.

The body of the elongated tubular member 310 can be cut from a hypotube or could be one or more outer jackets laminated, injection molded, or reflowed in to place. In one example, the elongated tubular member is cut from a hypotube having a high column strength, enabling good push and torque characteristics, the strain capacity for small bend radii, and high kink resistance. Commonly used hypotube materials include Nitinol and familiar stainless-steel alloys like 304 and 316. The elongated tubular member can have a uniform stiffness across its length, or a stiffness that varies along the length of the elongated tubular member. Variations in the stiffness profile of the catheter can be created by laser cutting features such as a circumferential slots or grooves and longitudinally- or axially offset patterned ridges or recesses can be machined In other instances, the elongated tubular member 310 can be made from a polymeric tube, or from one or more multi-durometer polymer jackets. During manufacture, the one or more jackets or sections of jackets could be fused using heat. Variations introduced into the axial or radial disposition of the jackets can tailor the axial and lateral stiffness profile from the proximal end to the distal end. For example, by configuring the jackets in an axial series, it is possible to transition the overall stiffness of the catheter from a stiffer proximal end to an extremely flexible distal end.

The surface of the polymeric tube can also be profiled with a series of ridges and recesses that afford enhanced torque, push, and trackability characteristics. Both the inner and outer surfaces of the catheter can be made from, or coated with, a lubricious low-friction material such as PTFE. This ensures when the catheter is navigated through the vasculature, there is a smooth, non-abrasive surface for contacting the interior vessel walls along the route to the target site.

To achieve a desired stiffness, other materials and/or additives having desired stiffness properties can also be used in the construction of the elongated tubular member. Materials and/or additives can be varied along the length of the elongated tubular member to create portions having differing stiffness, each portion being of a different stiffness or durometer. Additional layers or additives can be provided to control the individual stiffness of sections of the elongated tubular member. It is desirable, however, that axial stiffness transitions be relatively gradual, as otherwise the catheter could be biased to kink in regions of sharp flexibility change.

In a further example, the elongated tubular member 310 can have a proximal end, a distal end, an outer surface 316, and two inner surfaces. A first inner surface 115 can define an inner hollow lumen 114 for transmitting auxiliary devices or for transmitting aspiration or contrast. The first inner surface can be at least partially eccentric to the elongated tubular member. A second inner surface 119 can define an inflation lumen 117 extending therethrough which can assume an arc or crescent shape cross-section. In this way the inflation lumen can be smaller than the inner hollow lumen and take up less of the internal volume of the elongated tubular member.

FIG. 4 and FIG. 5 are cross-section views of the catheter tip of FIG. 3. FIG. 4 shows a cross-section view of the catheter tip through the inflated balloon 113. The respective profiles of the balloon lumen 126, the inflation lumen 117, and the inner hollow lumen 114 can be seen. The balloon can have a circular profile when inflated as shown or can take another shape as designed for a particular procedure.

The inflation lumen 117 can serve as a conduit for inflation media to inflate and deflate the balloon 113. The inflation lumen can connect to a port at the proximal end of the catheter, extend a majority of the length of the elongated tubular member, and empty in to the balloon lumen. The inflation lumen can have any number of shapes, including but not limited to a crescent shape of particular arc radius dimensions. The inflation lumen can be a sleeve of Polytetrafluoroethylene (PTFE), Polyethylene (PE), Polyethylene terephthalate (PET), fluorinated ethylene propylene (FEP), and the like.

The balloon can be constructed of any of a number of materials, such as Chronoprene, Polyurethane, Nylon, PBx, or another thermoplastic elastomer. These materials allow the balloon to be durable and thin. The balloon may or may not be gas-permeable since the design of the catheter does not require air to diffuse out of the balloon during preparation. The outer surface of the balloon can be coated with a hydrophilic coating for atraumatic lubricity, and the balloon can be shaped so that there is a minimal contact strip with the vessel wall when inflated.

Advancing through particularly tortuous vasculature can cause the catheter 110 and the associated lumens to kink or crimp. Kinking of the inner hollow lumen 114 can lead to binding on a guidewire or other devices. A kinked inflation lumen 117 can inhibit flow to and from the balloon of the balloon guide catheter, which can reduce the rate of or completely impede the inflation or deflation of the balloon.

In some extreme cases, a kinked inflation lumen can result in the complete failure of the balloon or loss of the ability to inflate or deflate the balloon. This can create complications during a treatment as the non-functioning balloon guide catheter may need to be removed, a physician may need to conduct a procedure without blood-flow arrest, or some other device may need to be inserted through the inflation lumen to deflate the balloon.

To combat kinking, the catheter profile can include a reinforcing wire configuration or braided mesh 318 along the length of the catheter tying an outer surface of the inflation sleeve 119 to an outer surface of the inner core 115, as seen in the cross-section views of FIG. 5. The reinforcing mesh can be encased within the polymeric tube of the elongated tubular member 310 and can act similar to rebar in preventing kinking of the catheter while maintaining a consistent lateral flexibility for steady trackability. The reinforcing mesh can be of a consistent structure and spacing along the axis of the catheter or can vary in shape and density along various lengths. For example, changing the mesh profile could increase flexibility of the distal end of the catheter while still minimizing the likelihood of kinking the inflation lumen. The strands can run in a substantially parallel fashion or in a crisscrossing configuration.

Other examples can change the braided mesh to a wire coil geometry to lower the flexural stiffness of the catheter 110 as compared to the braid. The density of the coils or the materials used in their construction can be adjusted to vary the axial stiffness profile of the catheter. The addition of the coils instead of the braid lessens this "whip" orientation around a sharp bend or loop in the vasculature.

The elongated tubular member 310 can also have an outer surface 316 that includes one or more outer jackets or liners providing a reduced friction surface. The jacket or jackets could be laminated, injection molded, or reflowed in to position. Both outer surface 316 of the elongated tubular member and the surfaces of the inner hollow lumen 114 can be coated with a lubricious low-friction coating, such as PTFE, high-density polyethylene, or a similar fluoropolymer. The coating can be applied via spray, plasma, or any other applicable method such that it is smooth and uniform. When the catheter is navigated through vasculature, the outer jacket can be effective to provide an even surface for gliding along the interior of blood vessels without harming or abrading the vessels or generating undue friction force that would resist the catheter being delivered to a treatment site. Similarly, a coating or liner on the inner hollow lumen would ease the advancement and navigation of other devices through the lumen.

In FIG. 6 is illustrated the luer 118 approximate the proximal end 121 of the balloon guide catheter. The luer can be a self-sealing connector with typical junctions for receiving attachments. The luer can be a rigid housing having a proximal end forming the proximal end 121 of the catheter, a distal end 211, an inflation port 210, and a mandrel hub 214. The housing of the luer is configured to be hermetically sealed while in use. The proximal end can serve as an inlet for other devices to be used in the endovascular procedure. The elongated tubular member 310, as seen in previous figures, can be proximally housed within the luer and can extend downstream from the distal end 211 of the luer. The inflation port 210 can branch radially away from the longitudinal body portion of the luer. The port can be sized to receive or transmit fluid, such as to or from a syringe. The luer can have a mandrel hub 214 as another stem off the body, and a removeable mandrel 216 can be disposed within the catheter to exit proximal the mandrel hub to the exterior of the luer 118. Actuation of the mandrel is accomplished by manipulating a mandrel tab 217 at the proximal end of the mandrel. The mandrel could be removed by tensioning the mandrel tab to slide the mandrel out from the mandrel hub.

The luer 118 shown in the FIG. 6 and other figures is used to illustrate a single aspect of the present design. Of course, so long as the mandrel is accommodated as described, the present design can be applied to other luers of a variety of shapes, sizes, and utility.

A view of the internals of the luer 118 without the removable mandrel is shown in FIG. 7. The luer can have an internal luer lumen 212 forming the hollow channel of the inflation port 210. The elongated tubular member 310 can be bonded or formed integrally with the luer housing. The elongated tubular member can originate and extend distally from a proximal end 314 in the housing. Access to the inflation lumen can be provided via an inflation inlet 222 passageway through the sidewall of, and approximate the proximal end of, the elongated tubular member 310. The inflation inlet provides a fluidic passageway between the luer lumen and the inflation lumen to allow the balloon to be inflated and deflated via the luer.

An air seal 218 can be disposed in the proximal end of the mandrel hub 214. The seal can be a compression gasket or other such methods known to the art. The proximal end of the seal can be flush with, extend from, or be recessed from the exterior surface of the mandrel hub. The air seal provides the utility of maintaining a pressure barrier and preventing air ingress to the luer even if the removable mandrel has been removed from the mandrel hub. The seal thus secures the internal catheter environment from contamination when the mandrel has performed its function. The seal can also prevent air bubbles from being entrapped during inflation or deflation of the balloon.

A detail view of the luer 118 internals of FIG. 7 with the mandrel 216 profile included is shown in FIG. 8. Prior to balloon inflation, at least a length of the mandrel 216 can extend through the air seal 218 of the mandrel hub proximal port 220 to exit the luer and provide an external gripping surface for the user. Internal to the luer, the mandrel can pass through the mandrel hub 214 and enter the inflation sleeve 119 of the elongated tubular member 310 via or proximal to the inflation inlet 222. The luer lumen 212 can act as a small-volume reservoir when the mandrel 216 is in place and blocking fluidic access to the inflation sleeve through the inflation inlet. The entrance of the mandrel into the inflation sleeve can occur proximal of or through the inflation inlet itself.

A detailed view of the interface around the inflation inlet 222 is also illustrated in FIG. 8. The mandrel 216 can be a flexible elastomer or other material with a high elastic strain limit such that it is sufficiently flexibly to bend in an arc as shown from the radially-offset mandrel hub 214 to the substantially longitudinal inflation sleeve 119 of the elongated tubular member 310. The inflation inlet can be shaped such that it facilitates this transitional bend. In one example, the longitudinal shape of the inflation inlet can taper such that when a mandrel is inserted and fed in to the catheter from the mandrel hub the distal end of the mandrel is funneled in to the inflation inlet and inflation lumen by the taper. From the inflation inlet, the mandrel continues distally in this "off-axis" configuration, occluding the full internal volume of the inflation lumen. In this way, the mandrel prevents any gas or other media from occupying the inflation lumen prior to use of the balloon guide catheter and initial inflation of the balloon.

A cross-section view of the elongated tubular member 310 from FIG. 8 distal and downstream of the inflation inlet is shown in FIG. 9. The elongated tubular member can be formed integrally with the luer or the outer surface 316 of the elongated tubular member can be bonded or press-fit inside the luer housing. The elongated tubular member can have at least two inner surfaces. A first inner surface can define the inner core 115 and inner hollow lumen 114 extending therethrough. A second inner surface can define the inflation sleeve 119 detailing the perimeter of the inflation lumen 117. As with other examples, the cross-section of the inflation lumen can be smaller than the cross-section of the inner hollow lumen. The inflation lumen 117, occupied by the mandrel 216 prior to balloon inflation, can be radially upwards, or "12 o'clock" orientation with respect to the inner core 115 and inner hollow lumen 114, or it can be at some other clocking orientation. The reinforcing braid or mesh 318 can have interlocking strands and extend around the outer surfaces of the inner core and inflation sleeve. The braid can take on a crossover configuration, a helical orientation, or some other means to reinforce and provide kink resistance for the catheter and lumens. The density of the reinforcing mesh can also be used to influence the stiffness properties of the catheter, allowing for a more longitudinally stiff proximally and a more flexible distal portion.

FIG. 10 also shows a cross-section view from FIG. 8 through the luer 118 housing and the elongated tubular member 310 at the axial location of the inflation inlet 222. The mandrel 216 occupies the crescent-shaped cross-section of the inflation sleeve 119 prior to balloon inflation. Because of the shape of the inflation lumen 117, the inner core 115 and the associated inner hollow lumen 114 are not concentric with the elongated tubular member 310. The cross-section of the inflation sleeve is crescent-shaped in this example, but if another shape is used for the inflation sleeve the mandrel area could be tailored for that geometry as well.

Figure 11A:
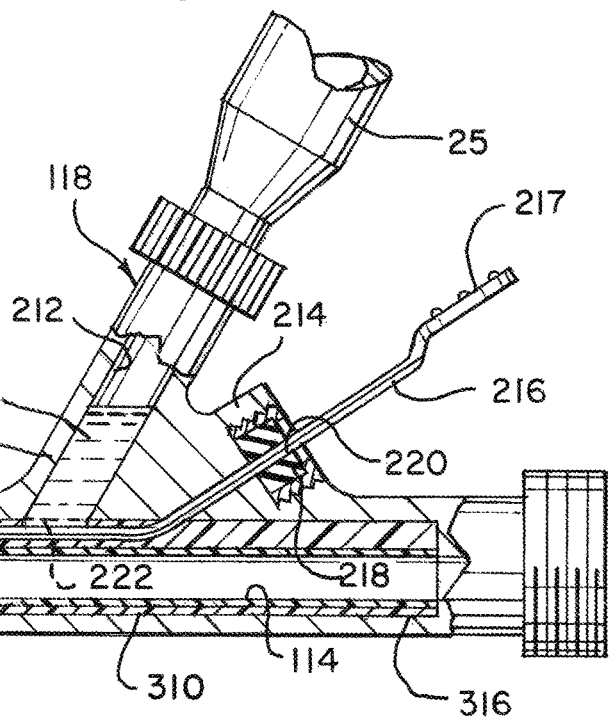
FIGS. 11A-11B are process views of the mandrel being withdrawn from the balloon guide catheter and inflation media filling the vacated inflation lumen according to aspects of the present invention.

When the balloon guide catheter has been advanced through the vasculature to the target site of an occlusive clot, the balloon can be inflated to arrest flow in the vessel and block off fluid proximal of the tip of the catheter. In most examples the seamless balloon is inflated inside the patient's vasculature using contrast media, saline, another neutral fluid, or a combination of these. Typically, an equal parts solution of contrast and saline is used. When the system is at a target site and the user is ready to inflate the balloon, a small amount of inflation media 26 can first be injected into the trunk of the inflation port 210 to pre-fill the luer lumen 212 via an inflation source or syringe 25 as shown in FIG. 11A. Pre-filling the luer lumen ensures that when the mandrel is removed from the catheter and the passage through the inflation inlet 222 to the inflation lumen 117 is opened, the evacuated space in the inflation lumen is filled with the contrast media from luer lumen.

Figure 11B:
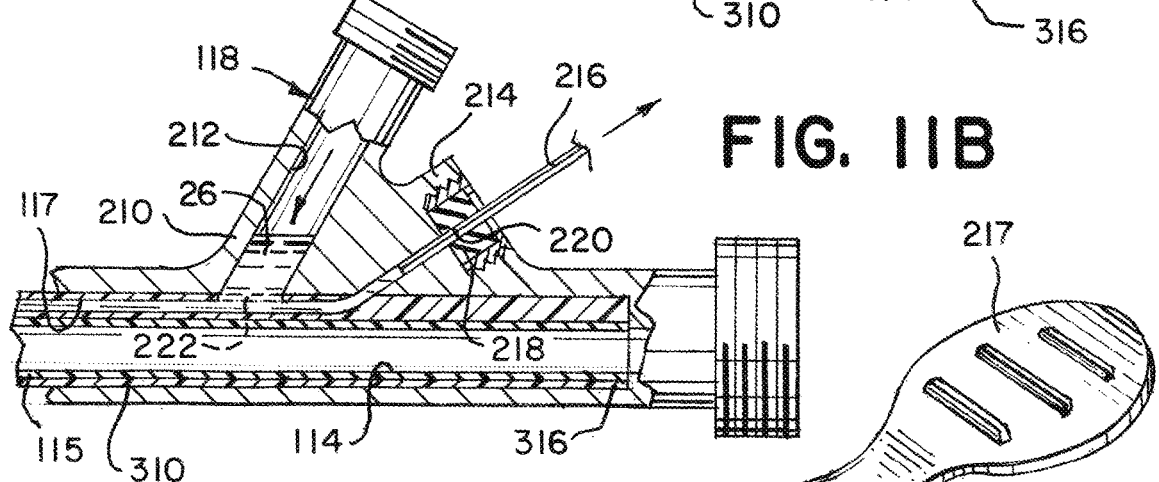

FIG. 11B illustrates the process of mandrel 216 removal when the operator is ready to inflate the balloon. The mandrel can be extracted proximally from the mandrel hub 214 of the luer 118 while the air seal 218 maintains the hermetic seal internal to the luer. When the mandrel body has cleared the inflation inlet 222 aperture through the wall thickness of the elongated tubular member 310, the volume of contrast media 26 in the lumen 212 of the inflation port 210 is drawn into the inflation lumen 117 by the negative pressure gradient left by the mandrel removal. This eliminates the steps otherwise required to purge air which would otherwise nominally occupy the inflation lumen. The inner hollow lumen 114 of the inner core 315 is not disturbed during this fluid transfer. The mandrel can either be completely removed from the luer, or the tail can be left at some internal position between the inflation inlet and the mandrel hub proximal port 220. At this point, further injection of inflation media into the inflation port will inflate the balloon. The fluid volume and/or pressure is held constant to keep the balloon engaged with the vascular lumen to prevent flow past the balloon. Once the procedure is complete, or to reposition the catheter, the balloon can be deflated by pulling the plunger of the syringe to draw out the media.

Figure 12:
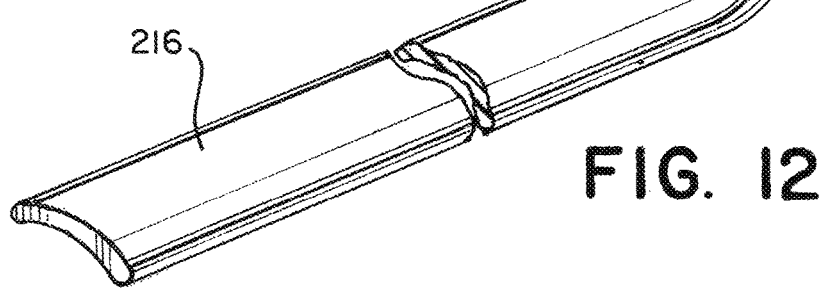
FIG. 12 is an isometric view of the mandrel independent of the balloon guide catheter according to aspects of the present invention.

FIG. 12 is an isometric view of the mandrel 216 independent of the catheter system. The main body of the mandrel can take the crescent shape of the inflation sleeve such that it occupies the full volume of the inflation lumen prior to balloon inflation. Navigation to the target site of the procedure can involve not only deflections, but also torqueing and small bend radii. As a result, the mandrel can be made from a highly-elastic, flexible material such that it can accommodate the associated strains imparted by the route and the catheter body. The mandrel tab 217 can be formed integrally with or independent from the mandrel. The tab can be any of a number of shapes so that it can easily be gripped and have features to provide positive tactile feedback to the user. In one example, the tab can have ridges or a diamond plate pattern for enhanced grip. The outer surface of the mandrel can be coated with a low-friction lubricious coating to enable it to slide more freely when withdrawn from the catheter in preparation to inflating the balloon.

Figure 13:
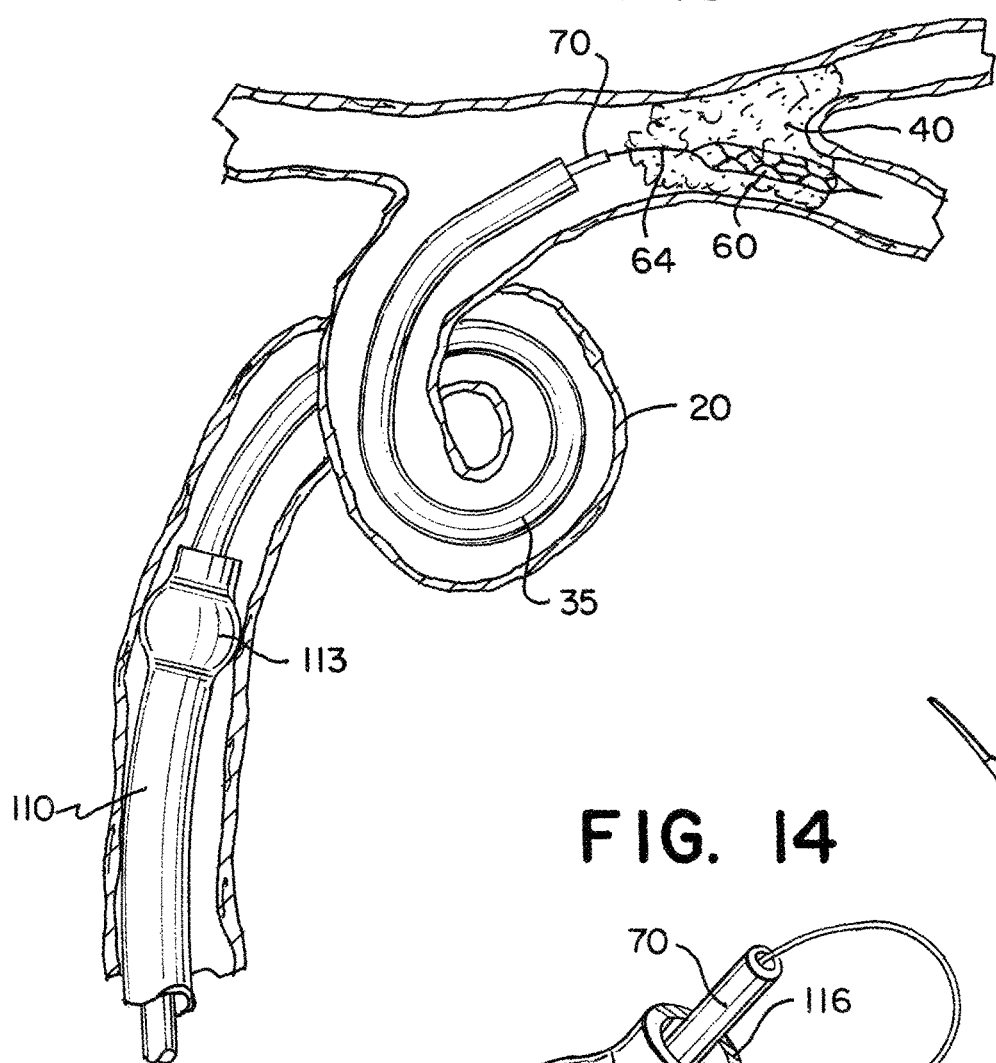
FIG. 13 illustrates the balloon guide catheter being used with an intermediate catheter, microcatheter, and clot retrieval device to capture a target occlusion in a blood vessel according to aspects of the present invention.

The present design for a balloon guide catheter requiring minimal preparation to inflate the balloon can also be used in conjunction with other mechanical thrombectomy equipment. Referring to FIG. 13, the balloon guide catheter 110 can be advanced through a target vessel 20 to a site proximal to an occlusive clot 40. The balloon 113 can be inflated to arrest proximal flow in the vessel. An access catheter, such as an intermediate catheter 35 or aspiration catheter can be advanced through and beyond the distal end of the balloon guide catheter to the target. A microcatheter 70 containing a clot retrieval device 60 can further be forwarded through the intermediate catheter and balloon guide catheter and deployed to capture the clot 40 while aspirating through one or more of the catheters. Upon capture of a clot, the clot retrieval device can be withdrawn into the intermediate catheter, which could compress the structure of the device and enhance the grip exerted on the clot during retrieval. The clot retrieval device 60, microcatheter 70, intermediate catheter 35, and clot 40 can then be withdrawn through the balloon guide catheter 110 and fully removed from the patient.

When the system is used in conjunction with other intermediate catheters or aspiration catheters, the system can use aspiration in conjunction with one or more flow restrictors or seals which can be selectively activated to project aspiration to the distal lumen of the desired catheter. The seals can be a hydrogel, an annular inflatable balloon-type member, take a molded O-ring profile, or could have a framework with a membrane covering. For example, the system could be provided with an intermediate catheter 35 disposed within the balloon guide catheter 110, as seen in FIG. 13. If aspiration is applied to the proximal lumen of the balloon guide catheter and a circumferential seal is activated between the outer surface of the intermediate catheter and the inner surface of the balloon guide catheter, the full force of the aspiration can be translated to the distal tip of the intermediate catheter. Similarly, if no seal is activated, aspiration will be split between the intermediate catheter 35 and the balloon guide catheter 110.

The clot retrieval device 60 mentioned in this description can be any of a number of commercially available products, and many of those share many common features. Some devices compress the clot upon capture to gain a firm grip, but this tends to make the clot firmer, or "stickier", which can complicate retrieval. Other devices seek to expand between the clot and the vessel in such a way as to minimize compression while loosening the clot from the vessel wall. Often, such devices can be made from Nitinol or another shape-memory material with sufficient elastic strain capacity such that the elastic limit would not be exceeded when the device 60 was in the collapsed delivery configuration within a microcatheter 70. This elastic strain capacity allows the device to be effectively "spring loaded" within the microcatheter so that it can self-expand to engage a clot when deployed out of the distal end of the microcatheter catheter.

Placement of the balloon guide catheter during procedures can be aided by the addition of radiopaque markers, as is well known in the art. Such markers can include radiopaque alloying elements such as palladium, platinum, gold, etc. For example, a radiopaque marker could be placed distal of the balloon at the distal tip of the catheter. Markers could be placed on the inner core to mark the terminal ends of the balloon during the procedure.

Figure 14:
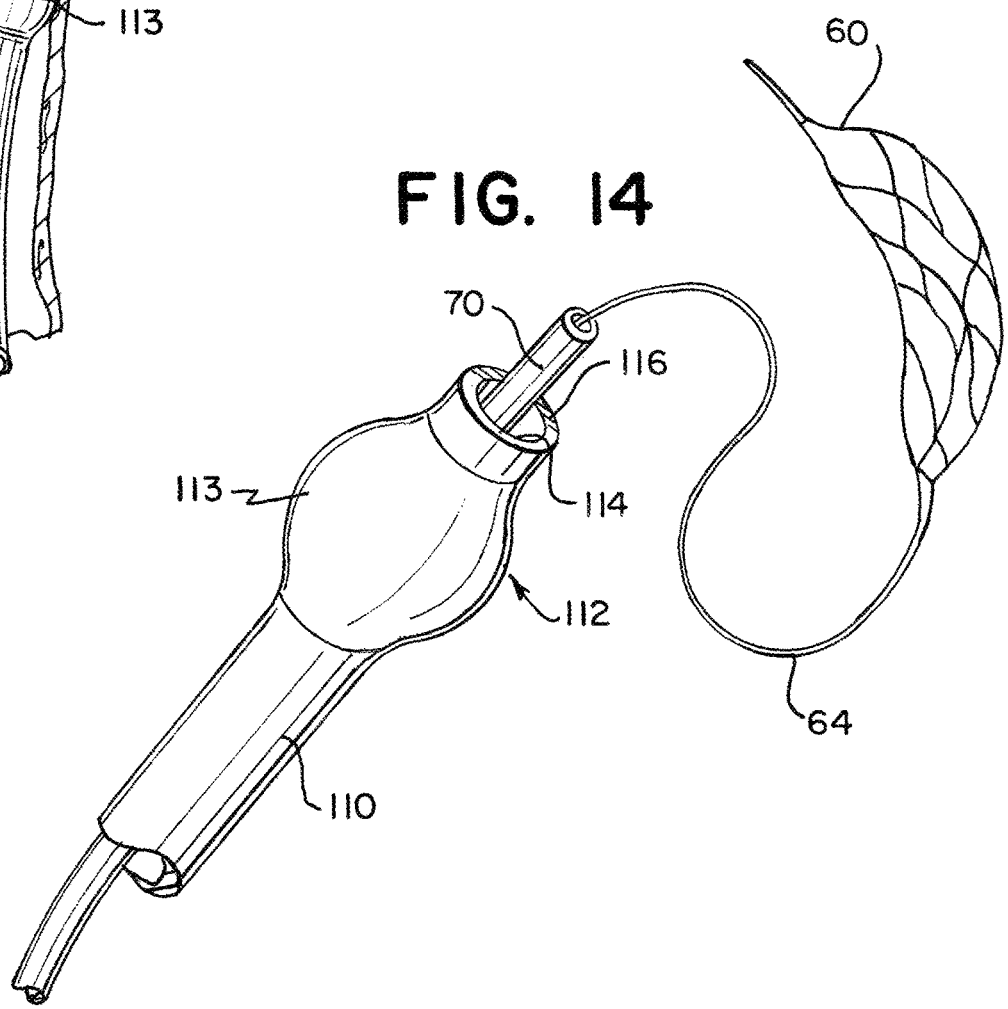
FIG. 14 illustrates the tip of the balloon guide catheter with a microcatheter and clot retrieval device according to aspects of the present invention.

In another example, the balloon guide catheter 110 can be maneuvered to the internal carotid artery, the balloon 113 can be inflated, and the microcatheter 70 and clot retrieval device 60 can be advanced through the lumen 114 and deployed directly from the distal end 116 of the balloon guide catheter tip 112. This standard practice is illustrated in FIG. 14. The balloon can be inflated using the process already described in this description. The inflated balloon blocks off blood proximal to the target location from interfering with the capture of the clot, and aspiration can be applied through the balloon guide catheter to prevent the distal migration of fragments or debris from the target site. If additional retrieval attempts are needed to clear the vessel, the microcatheter 70 and clot retrieval device 60 can be quickly delivered back to the target site.

FIG. 15 and FIG. 16 are flow diagrams each comprising method steps for performing a mechanical thrombectomy procedure with such a system. The method steps can be implemented by any of the example systems, devices, and/or apparatus described herein or by a means that would be known to one of ordinary skill in the art. The method steps described can be performed efficiently without the associated laborious purging steps associated with other balloon guide catheter systems.

Referring to a method 1500 outlined in FIG. 15, step 1510 describes the task of selecting a balloon guide catheter for a mechanical thrombectomy procedure. The balloon guide catheter can have a proximal end, a distal end, an inner hollow lumen, and a proximal luer having a luer lumen. In addition, the catheter can have an inflation sleeve defining an inflation lumen separate from the inner hollow lumen and a balloon for flow arrest and efficient aspiration at a target site. In step 1520, an air seal can be disposed in a mandrel hub of the luer to prevent air other contaminants from entering the luer lumen. The sealing can be accomplished through any of a number of methods known in the art for hermetically sealing medical devices. In step 1530, a removable mandrel is disposed through the air seal which extends distally occupying the full volume of the inflation lumen, precluding the presence of trapped gas in the system prior to inflation. Step 1540 provides for gaining access to an arterial blood vessel of a patient using conventional, well-known techniques. In step 1550, the balloon guide catheter is advanced into and through the vasculature to a location proximal of an occlusive clot using methods common in the art. In step 1560, the luer lumen can be filled with a small amount of inflation media through the inflation port of the luer. This step can be accomplished by injecting a fraction of the inflation media from a filled syringe. As an alternative, this step could involve venting the luer lumen with a gas-permeable membrane.

Referring the method 1600 outlined in FIG. 16, in step 1610 the user can pull a proximal tab of the mandrel to extract the mandrel from the catheter and draw a vacuum in the inflation lumen. The inflation media in the luer lumen is thus drawn in to the inflation lumen. The balloon can then be inflated by injecting additional inflation media through the inflation port of the luer in step 1620.

Once the balloon is fully deployed, the occlusive clot can sometimes be removed by aspirating directly through the balloon guide catheter, as with large distal internal carotid artery (ICA) occlusions. In many cases, though, the next steps involve variations using other means to retrieve the clot in the mechanical thrombectomy procedure. Such procedures are well known in the art and the steps herein are not meant to be an exhaustive list. In step 1630, an intermediate catheter can be advanced through the balloon guide catheter to the target location and used to aspirate an occlusive thrombus. An alternative in step 1640 involves advancing a microcatheter and a clot retrieval device through the balloon guide catheter to the target location and deploying the clot retrieval device to capture the occlusive thrombus accompanied by aspiration. In another example in step 1650, an intermediate catheter is advanced through the balloon guide catheter and a microcatheter and clot retrieval device are advanced through the intermediate catheter to the target location. The microcatheter and clot retrieval device are advanced across a thrombus and the clot retrieval device deployed to capture the thrombus accompanied by aspiration through one or more of the catheters. In step 1660, flow reversal is achieved by aspiration directed through the balloon guide catheter as a thrombus is retrieved.

The invention is not limited to the examples described, which can be varied in construction and detail. The terms "distal" and "proximal" are used throughout the preceding description and are meant to refer to a positions and directions relative to a treating physician. As such, "distal" or "distally" refer to a position distant to or a direction away from the physician. Similarly, "proximal" or "proximally" refer to a position near to or a direction towards the physician.

In describing examples, terminology has been resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "patient" or "subject" can be a human or any animal. It should be appreciated that an animal can be a variety of any applicable type, including, but not limited to, mammal, veterinarian animal, livestock animal or pet-type animal, etc. As an example, the animal can be a laboratory animal specifically selected to have certain characteristics similar to a human (e.g., rat, dog, pig, monkey, or the like).

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It must also be noted that, as used in the specification and the appended claims, the singular forms "a," "an," and "the" include plural referents unless the context clearly dictates otherwise. Ranges can be expressed herein as from "about" or "approximately" one particular value and/or to "about" or "approximately" another particular value. When such a range is expressed, other exemplary embodiments include from the one particular value and/or to the other particular value.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

The descriptions contained herein are examples of embodiments of the invention and are not intended in any way to limit the scope of the invention. While particular examples of the present invention are described, various modifications to devices and methods can be made without departing from the scope and spirit of the invention. For example, while the examples described herein refer to particular components, the invention includes other examples utilizing various combinations of components to achieve a described functionality, utilizing alternative materials to achieve a described functionality, combining components from the various examples, combining components from the various example with known components, etc. The invention contemplates substitutions of component parts illustrated herein with other well-known and commercially-available products. To those having ordinary skill in the art to which this invention relates, these modifications are often apparent and are intended to be within the scope of the claims which follow.

The invention claimed is:

1. A system for preparing a balloon guide catheter, the system comprising:
    a catheter, comprising:
        a substantially tubular inner core having an inner hollow lumen; and
        an elongated tubular member disposed around the inner core and comprising an inflation sleeve having an inflation lumen extending therethrough, the elongated tubular member and inflation sleeve extending a majority of the length of the tubular inner core;
    a proximal luer comprising:
        a proximal end and a distal end;
        an internal luer lumen;
        an inflation port in fluidic communication with the luer lumen; and
        a mandrel hub having a proximal port, the mandrel hub in fluidic communication with the luer lumen;
    a mandrel removably disposed within the mandrel hub and the inflation sleeve, the mandrel occupying the full volume of the inflation lumen and further comprising a tab extending proximally from the proximal port of the mandrel hub external to the proximal luer configured to enable the removal of the mandrel from the mandrel hub and the full volume of the inflation lumen; and a balloon in fluid communication with the inflation lumen of the inflation sleeve.

2. The system of claim 1, further comprising an inflation inlet in fluidic communication with the luer lumen and with the inflation lumen.

3. The system of claim 2, wherein the mandrel is configured to be removed from the mandrel hub prior to inflation of the balloon to create a vacuum in the inflation lumen, and wherein inflation media from the luer lumen fills the inflation lumen along the length of the catheter.

4. The system of claim 2, wherein the proximal port of the mandrel hub comprises an air seal preventing air ingress to the inflation lumen.

5. The system of claim 1, wherein the inflation lumen is smaller than the inner hollow lumen.

6. The system of claim 1, wherein the inflation sleeve comprises a substantially crescent-shape cross-section.

7. The system of claim 1, wherein the balloon is affixed to a distal portion of the tubular inner core.

8. The system of claim 1, wherein the elongated tubular member is configured to be at least partially eccentric to the tubular inner core.

9. A system for preparing a balloon guide catheter, the system comprising:

a catheter, comprising:
an elongated tubular member comprising:
a proximal end;
a distal end;
an outer surface; and
a first inner surface defining an inner hollow lumen extending therethrough, the inner hollow lumen at least partially eccentric to the elongated tubular member;
a second inner surface defining an inflation lumen extending therethrough;
a proximal luer comprising:
an inner lumen;
an inflation port sized to receive fluid injection;
a mandrel hub sized to receive a mandrel; and
an air seal disposed in the mandrel hub preventing air ingress to the inflation lumen of the elongated tubular member;
a mandrel removably disposed within the mandrel hub and further comprising a tab extending proximally from the proximal port of the mandrel hub external to the luer configured to enable the removal of the mandrel from the mandrel hub and the full volume of the inflation lumen; and
a seamless balloon in fluidic communication with the inflation lumen.

10. The system of claim 9, wherein the seamless balloon is secured to the distal end of the elongated tubular member.

11. The system of claim 9, wherein the mandrel is shaped to occlude a full cross-section of the inflation lumen.

12. The system of claim 9, wherein the inflation lumen is smaller than the inner hollow lumen.

13. The system of claim 9, wherein the inflation lumen comprises a substantially crescent-shape cross-section.

14. The system of claim 9, further comprising an inlet approximate a proximal end of the elongated tubular member, the inlet providing a fluidic passageway between the inflation lumen and the inner lumen of the proximal luer.

15. The system of claim 14, wherein the mandrel is sized to occupy the full volume of the inflation lumen and is configured to be removed from the mandrel hub prior to inflation of the balloon to create a vacuum in the inflation lumen, and wherein inflation media from the luer lumen fills the inflation lumen along the length of the catheter.

16. A method for preparing a balloon guide catheter, the method comprising:

selecting a balloon guide catheter having a proximal end and a distal end, an inner hollow lumen, an inflation sleeve defining an inflation lumen, a balloon, and a proximal luer having a luer lumen;
positioning an air seal within a mandrel hub of the luer which prevents air ingress to the luer lumen;
disposing a removeable mandrel through the air seal in the mandrel hub and extending the removeable mandrel distally to occupy the full volume of the inflation lumen, the removable mandrel comprising a proximal tab;
accessing a patient's vasculature using conventionally-known techniques;
advancing the balloon guide catheter into the vasculature;
filling the luer lumen with an inflation media through an inflation port of the proximal luer;
creating a vacuum in the inflation lumen by pulling the proximal tab to extract the mandrel from the mandrel hub so that the inflation media from the luer lumen fills the inflation lumen along the length of the catheter; and
inflating the balloon by injecting the inflation media through the inflation port of the luer proximal luer.

17. The method of claim 16, further comprising the step of advancing an intermediate catheter through the balloon guide catheter to the target location and aspirating an occlusive thrombus.

18. The method of claim 16, further comprising the step of advancing a microcatheter and clot retrieval device through the balloon guide catheter to the target location and deploying the clot retrieval device to capture an occlusive thrombus and retrieve the thrombus with aspiration.

19. The method of claim 16, further comprising the step of advancing an intermediate catheter, microcatheter, and clot retrieval device through the balloon guide catheter to the target location and deploying the clot retrieval device to capture an occlusive thrombus and retrieve the thrombus with aspiration.

20. The method of claim 16, further comprising the step of aspirating through the balloon guide catheter as an occlusive thrombus is retrieved.

* * * * *